United States Patent [19]

Kossmann

[11] Patent Number: 5,766,538
[45] Date of Patent: Jun. 16, 1998

[54] METHOD OF QUALITY CONTROL DURING PRODUCTION OF CONCRETE BLOCKS

[75] Inventor: Olga Kossmann, Weissenthurm, Germany

[73] Assignee: Masa Aktiengesellschaft, Andernach, Germany

[21] Appl. No.: 565,069

[22] Filed: Mar. 28, 1995

[30] Foreign Application Priority Data

Mar. 28, 1995 [DE] Germany .................... 195 11 324.1

[51] Int. Cl.[6] .................................................. B28B 3/00
[52] U.S. Cl. ..................... 264/407; 264/409; 264/411; 264/40.4
[58] Field of Search .......................... 264/407–409, 264/411, 40.1, 40.4

[56] References Cited

U.S. PATENT DOCUMENTS 4,095,925  6/1978  Cruzen et al. ............... 425/141

FOREIGN PATENT DOCUMENTS

| 0 343 033 | 11/1989 | European Pat. Off. . |
|---|---|---|
| 0 657 260 | 6/1995 | European Pat. Off. . |
| 35 30 681 | 3/1987 | Germany . |
| 42 00 801 | 8/1993 | Germany . |
| 2179588 | 3/1987 | United Kingdom . |

Primary Examiner—Karen Aftergut
Attorney, Agent, or Firm—Michael J. Striker

[57] ABSTRACT

In a method for quality control during production of concrete blocks by bringing a concrete mortar into an upwardly open hollow mold with a solid peripheral wall for forming at least one molded blank placed on a flat supporting surface, a thickness of a molded blank is determined contact-free for testing the dimensional stability. The volume of the molded blank is determined from the determined thickness and the cross-section of the hollow mold. The density is obtained from the weight and volume, which is a criteria for strength and resistance testing of the molded blank. Finally, the appearance of the molded blank is determined by at least one video camera and compared with the appearance of faulty molded blank to determine the molded blanks with surface errors. All results of the height, density and surface measurements can be used for control of the production arrangement.

11 Claims, 1 Drawing Sheet

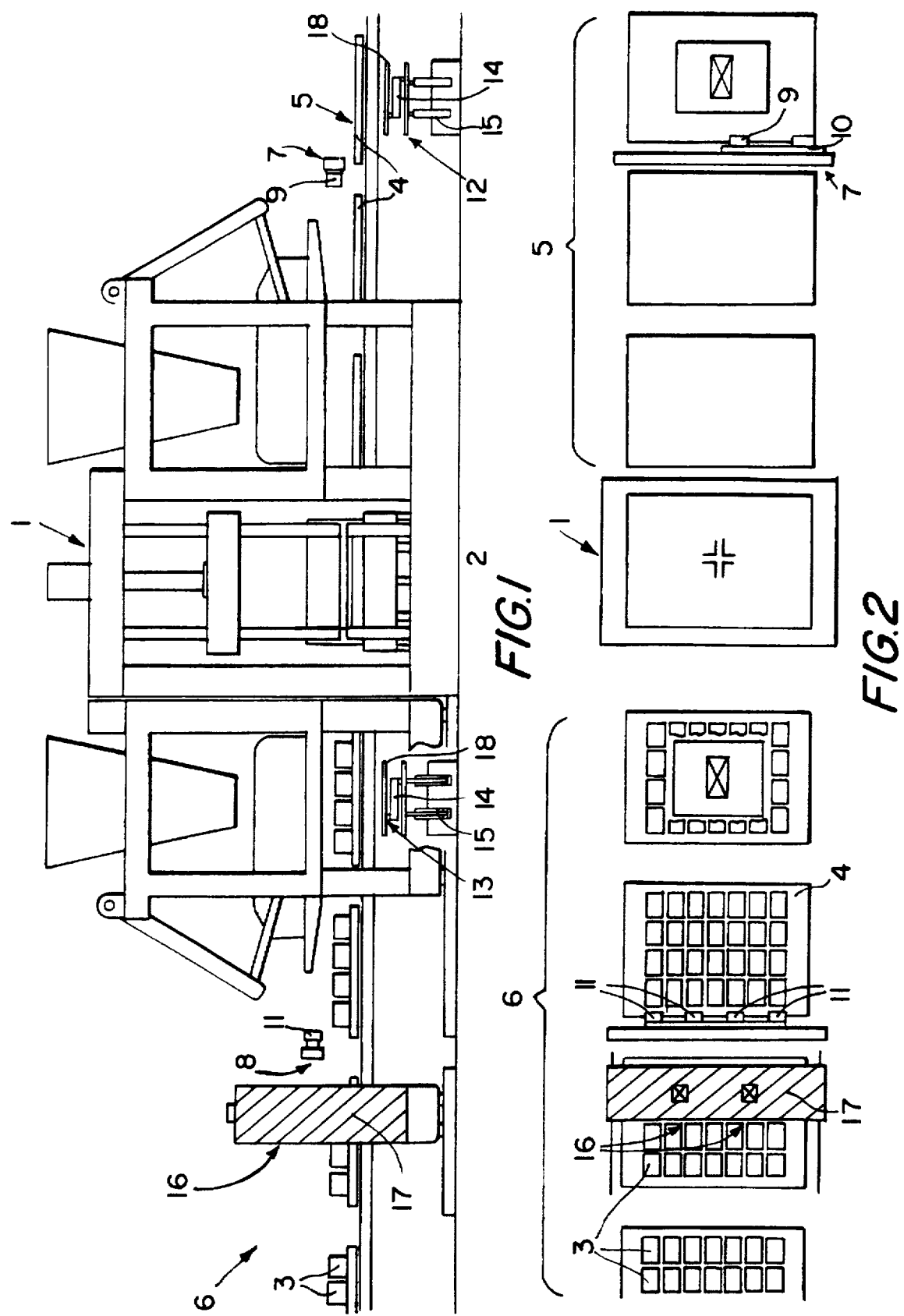

METHOD OF QUALITY CONTROL DURING PRODUCTION OF CONCRETE BLOCKS

BACKGROUND OF THE INVENTION

The present invention relates to a method of quality control of concrete blocks as well as to an apparatus for producing and controlling concrete blocks.

Concrete blocks, in particular concrete pavement blocks are produced by vibration or corresponding filling a hollow mold with concrete mixture and compressing the same. In this way molded blanks are produced which substantially correspond to the sizes of the concrete block to be made. However they are form-stable only when they are placed on a substrate and carefully transported to maintain their shape. They are not suitable for taking up mechanical forces or chemical loads which can be withstood by the finished, completely hardened concrete blocks.

In a production apparatus for producing such molded blanks, empty plates, or in other words boards and sheets are supplied to a first transporting device, several molded blanks are placed on the plates in the production apparatus in a matrix arrangement, and the plates filled with the molded blanks are moved to a second transporting device from the production apparatus and deposited for drying and hardening.

Concrete blocks, in particular pavement blocks of concrete must satisfy certain quality requirements which are outlined for example in German and also European standards. They include a prescribed breakage and cracking average strength, a prescribed resistance against the action of frost and dew salt as well as prescribed surface property (no cracks, etc.).

From these quality properties, in all cases the surface property must be tested in moist molded blanks. During the testing of dimension stability with conventional methods, the testing arm of gauges and the like deforms the soft concrete and therefore damages the molded blank, instead of testing the same. A testing of strength as well as of the frost and dew salt resistance requires a multi-week, complete hardening of the concrete block. A conventional strength testing on soft molded blank does not make any sense.

A feedback between a found error and operational parameters which are dominant during the production of the molded blanks is possible therefore with a multi-week delay. When a falsely adjusted operational parameter leads to unacceptable low strength, then with the production of several weeks reject or reduced quality occurs.

The testing of the surface property is usually performed by a personnel who examine concrete blocks or molded blanks supplied for testing. Individual fluctuations as well as the action of inattentiveness are unavoidable. Finally, personnel who is entrusted with the testing must be reliably and sufficiently qualified. Therefore, from the reasons of saving the continuous disturbance free testing of all produced concrete blocks is not performed, and it is limited only to individual probes within the prescribed standards.

The testing of the strength as well as the frost and dew salt strength is therefore intermittent and can be performed in a sampling fashion. Moreover, it is time consuming and requires expensive testing devices.

SUMMARY OF THE INVENTION

Accordingly, it is an object of the present invention to provide a method of and an apparatus for quality control of concrete blocks which avoids the disadvantages of the prior art.

In keeping with these objects and with others which will become apparent hereinafter, one feature of the present invention resides, briefly stated, in a method of quality control in accordance with which for controlling a dimension stability, the position of an upper limiting surface of at least one molded blank over a supporting surface is determined in a contact-free manner, and from this position a thickness of the molded blank is determined.

It is another feature of the present invention to provide an apparatus for quality control which has means for supporting of molded blanks and having supporting surface, means for contactlessly determining a position of an upper limiting surface of at least one molded blank over the supporting surface, and means for determining a thickness of the molded blank from this position.

When the method is performed and the apparatus is designed in accordance with the present invention, a testing of at least one of the above mentioned quality criteria is performed directly in the production arrangement, and the testing is performed so that individual deviations of the testing personnel are excluded and in each case the testing is performed uninterruptedly.

The present invention proceeds from the recognition that the peripheral part of the upwardly and downwardly flat paving blank molded from the hollow mold as well as its basic surface which is also molded by deformation of the upper surface of a plate are dimensionally stable, and conventionally during testing of dimensional stability were not rejected as a rule.

The only critical parameter is the thickness of the block which does not depend from the geometry of the hollow mold, but instead depends on the quantity of mortar which fills the hollow mold, its composition, and its compression degree. For this reason in accordance with the present invention only the thickness of the molded blank is determined by contact-free determination of the height of its upper, horizontally oriented surface. Basically, this single position determination is sufficient since the lower surface of the molded blank is placed on a support which is referred to the machine and its height therefore can be determined.

Since the supporting surface is formed by the above mentioned plates which can have different wear degree and therefore different thickness, it is proposed in accordance with a further embodiment of the present invention to determine also the height of the supporting surface, and the difference between both heights therefore corresponds to the thickness of the corresponding molded blank.

The determination of the height of the supporting surface is performed preferably in a contact-free manner, in order to avoid an error which can be caused by dirtying or wear of a contact sensor.

It is basically possible to determine at the same measuring place of the plate the upper surface of the molded blank and a point of the supporting surface which is not occupied by the molded blank. It is preferable to scan however the supporting surface of the empty plate, with the concomitant advantage that a very great part of the supporting surface can be detected. When the measuring values received one after the other substantially deviate from one another, this means that the corresponding plate is uneven, or in other words dirty or bent. Thereby the scanning of the supporting surface is performed by a series of measurements in accordance with a further advantageous embodiment of the invention.

When the measuring sensor for the determination of the supporting surface is arranged sufficiently far from the production arrangement, it is advantageous when the plate before reaching the production arrangement of the first transporting device is removed and then cleaned, oriented or eliminated. It is guaranteed that the lower surface of the molded blank is always formed flat. Errors of the molded blank which results from the uneven supporting surface are therefore excluded.

The determination of the supporting surface is performed by a first position measuring sensor device which is preferably movable relative to the plate and transversely to the transporting direction of the first transporting device. The plate or its supporting surface can be scanned substantially diagonally. This scanning process is basically sufficient and preferable. It is also however possible to provide the position measuring sensor device with so many sensors located near one another or to guide them over the supporting surface over such a densely arranged tracks that the whole supporting surface can be scanned uninterruptedly.

The utilized sensors are preferably ultrasound sensors which send an ultrasound signal and receive its echo. The distance through the measurement object is calculated from the time delay of the echo. The position of the supporting surface whose distance is determined is relatively great so that each sensor during its relative movement to the supporting surface scans a relatively wide surface band and thereby scans a greater part of the upper surface than is possible with a sensor provided for determination of a smaller surface.

The measurement accuracy of an ultrasound sensor is sufficient basically for smooth and flat supporting surfaces.

A second position measuring device is provided either in the production arrangement or on the second transporting device for measurements of the position of the upper surface of the molded blank. Preferably a relative movement is provided during the measurements between them, so that the above mentioned upper surfaces can be scanned linearly by successive measurements.

Since the molded blanks as a rule are supported on the plate in several rows which are parallel to the transporting direction, it is advantageous to associate a single sensor which each of said rows, so that preferably all molded blanks can be determined as to their thickness in a contact-free manner. When in the production arrangement due to a disturbance the hollow space of the hollow mold corresponding to a special molded blank is filled inadequately, then this disturbance is determined on the machine since the thickness of the associated molded blank is too small. It can be lifted in earliest possible time without producing a number of rejected blocks which or individual rejected blocks are supplied undetected together with error-free blocks.

The sensors used in the last mentioned measurement are preferably laser sensors. They make possible a very accurate measurement and moreover have a very narrow measuring field, so that they recognize broken edges or similar errors and can also recognize unacceptable position deviations.

Especially important is however the inventive determination of the strength properties and the properties of the chemical resistance of the concrete block produced from the molded blank.

The invention is based on the recognition that the above mentioned properties are located within a permissible region when the thickness of the molded blank is located within a predetermined region. The invention proceeds in other words from the recognition that a soft molded blank with a predetermined thickness produces as a rule a sufficiently solid and chemically resistant concrete block. Substantial studies have shown that the blocks which have faults in strength or resistance also have faulty concrete composition which in moist condition of the molded blank differs from the right composition by a different density.

Since the peripheral edges of the block and therefore its cross-sectional surface is determined because of geometry of the hollow mold and since the thickness of the block can be determined by the above mentioned processes, it is possible to determine the volumes of all blocks located in a plate with good accuracy. The critical magnitude of the thickness can be determined very simply with the above described required dimensional stability testing.

In accordance with the present invention the plate before and after loading with the molded blanks is moved in a continuous manufacturing process. The weighing stations are provided in the first and the second transporting device, and the weight supplied together with the already determined volumes provides the density of the soft material which forms the molded blanks.

It is of course possible to weigh the molded blanks without the plate, so that a single weighing step is necessary.

If the density deviates from its nominal value, for example due to a disturbance in the production arrangement, then it can be stopped, adjusted and in some cases repaired. The rejects which are produced in such cases in the known arrangements are avoided. Instead, there is only a reject of the molded blanks of one plate or in some cases several plates.

With the present invention instead of the conventional destructive testing of individual, finishes concrete blocks a destruction-free testing of all molded blanks is provided. In particular, it is performed at the stage of the manufacture in which they are soft, coming straight from a production arrangement, so that not the strength of chemical resistance itself, but instead parameters which are connected with them, are determined.

The testing can also be performed when a molded blank or several molding blanks have faulty thickness, since it is determined and supplied for computation of the right volume. The unavoidable tolerances during all measurements are so low that the density can be determined with sufficient accuracy.

For further improvement of the measuring accuracy, it is proposed in accordance with a further embodiment of the present invention to provide a measurement of whether the plate loaded with molded blanks unduly sags or not. It is here possible and in some cases advantageous to measure the height of the lower surface of the plate before and after the loading with molded blanks, for example by a distance sensor with ultrasound or a laser beam. It is however also possible to determine the height of the edge in the center of the lower side of the plate at the location which is preferably associated with the weight determination of the plate loaded with the molded blanks. It is finally also possible to determine the height near the center of the supporting surface at a location which is not loaded with molded blanks or in other words from above, and compare with the height of the same location of the loaded plate. This process provides the most accurate measuring results.

If it is determined that when a sagging exceeds a permissible value, then the corresponding plate can be removed. It is however possible with the sagging of the plate in or near its center to calculate the course of its supporting surface and to take it into consideration during the thickness determination of the molded blank.

As to the testing of the surface property of the molded blank, it is performed from the recognition that here as in the dimensional stability testing, the upper surface of the molded blank forms a critical upper surface. If this surface is fault-free in particular with orderly composition and thereby density of the material of the molded blank, then as a rule the other surfaces of the molded blank or the later concrete block will not be rejected.

In accordance with the present invention the molded blank supported on the plate is observed from above with at least one video camera and the image or each produced image is compared with a stored images of faulty molding blanks or the stored image of the fault-free molded blanks. Coincidence with an image of a faulty molded blank or non-coincidence with an image of a fault-free molded blank is determined, for example by means of an alarm device.

Preferably, several video cameras are provided, and preferably there is a relative speed between the video cameras during the testing, so that in each measurement an image portion is detected by a video camera which shows several molded blanks. In the case of a failure indication, the group of molded blanks can also be determined, in which at least one fault-free surface occurs.

In order ensure a maximum reproducible and optimal observation of the molded blanks, an illumination device is associated with the video camera or each video camera. It is further advantageous to provide a screen such as for example a tunnel, in which the video camera or cameras and the illuminating device or devices are arranged to screen the outside light and to run over the corresponding plate.

The features of the inventive apparatus are derived from the above presented information. For the added determination, preferably two way stations are provided so that one weighing station is arranged in the first transporting device for the empty plates and another weighing station is arranged in the second transporting device for the full plate. In the associated signal processing device, it is provided that during the measurement of the thickness of the molded blank, both measurements which are performed on the same plate before and after the production of the arrangement are associated reliably with one another.

At least one load sensor, preferably a pressure cell is provided in each weighing station. Its measuring region corresponds to the weight of the empty or full plate, so that a maximum accurate weighing is provided.

For avoiding the situation when the transporting forces from one of the transporting devices influence the weighing, the plate to be weighed is lowered onto the corresponding weighing device and sits preferable on a platform for centering the forces which occur non-centrally and supplying the same centrally into the load sensor. A lifting device is provided preferably for lowering of the plate and arranged under the load sensor. It lowers and lifts the platform and the plate.

Preferably also a device is provided which provides the above mentioned measurement of bending of the plate loaded with the molded blanks. Preferably this arrangement is associated with the second weighing station.

The measurements can be performing on the upper side or on the lower side of the plate. Preferably, it is performed contact-free with a distance sensor operating with ultrasound or a laser beam.

The signal output of this distance sensor or distance sensors is connected with an evaluating device. The evaluating device during occurrence of such a sagging of the plate which falsifies the measurement of the thickness of the molded blank in unacceptable manner, either causes a corresponding plate to be rejected, or calculates from the sagging the course of the downwardly bent surface of the plate and with the computation results corrects the thickness measurements on the individual molded blank.

All measurement results are supplied to a processing and evaluating device in which the above described comparison of the detected or calculated values with nominal values is performed. In the case of unacceptable deviations, an alarm device can be released, and substantially simultaneously a monitor represents an accurate determination of the detected error.

The processing and evaluating device can be however used for controlling the production device, so as to stop or to regulate it during occurrence of a predetermined fault. In other words, it provides such a control that the detected fault is either removed or compensated.

The above mentioned method steps and apparatus features for testing of individual parameters are all used together to make possible an exhausting testing of the molded blanks. It can be also utilized when only an individual parameter must be determined.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a side view of a device for producing concrete blocks with a quality control in accordance with the present invention; and FIG. 2 is a plan view of the device of FIG. 1.

DESCRIPTION OF THE PREFERRED EMBODIMENTS

The shown apparatus includes a known production arrangement 1 which has a hollow mold 2 for molding molded blanks 3 arranged in a matrix on a plate, a sheet, a board 4 and the like.

The empty plates 4 are placed successively in a known manner on a first transporting device 5 in the production arrangement 1. There the molded blanks 3 are molded on the plate 4 and the plate 4 provided with the molded blanks 3 leaves the production arrangement 1 to a second transporting device 6.

An ultrasound measuring device 7 is arranged on the first transporting device 5. It is composed of a traverse which extends transversely to the transporting direction of the first transporting device 5. Two or three ultrasound sensors 9 with analogous output are mounted on the traverse on a support 10 which moves along it. The ultrasound sensors 9 have a measuring region of 50–200 mm and transmit in this region a voltage of 1.5–7.5 V proportional to a measured distance.

The accuracy of these sensors amounts to 0.2 mm. The sensors 9 send an ultrasound bundle which is reflected on the surface of the plate 4 located under the ultrasound measuring device 7, and then again received by the corresponding sensor 9. The sensor 9 calculates the distance from the running time.

The plate 4 moves in a transporting device under the ultrasound measuring device 7. The sensors 9 move with the support 10 by a pneumatic cylinder without a piston rod. The surface of the plate 4 is scanned diagonally in adjacent tracks.

At the start of the measurements all 20 ms a measuring value is taken from the sensors 9 and stored. From the determined measuring values, an average value is calculated which is also stored. The plate thickness is determined from this measuring value and a reference measurement performed during adjustment of the device and representing the height of the sensors 9 over the transporting device 5. This plate thickness forms a correction value during the above described measurement.

A laser measuring device 8 is arranged after the production arrangement 1 over the second transporting device 6. It is composed of a traverse which extends transversely to the transporting direction and carries a number of laser sensors 11, preferably five, which are arranged near one another. They operate in accordance with a triangulation principle. Each laser sensor 11 sense a laser beam which is reflected on the upper surface of corresponding molded blank 3 to a location of the sensor 11 whose position is representative for the distance of the reflecting surface from the sensor 11. The measuring region of the utilized sensors amounts to 50–100 mm, the measuring accuracy amounts to 0.1 mm, and a voltage proportional to the measuring value amounts to 0–10 V.

Preferably, the molded blanks 3 are placed on each plate in a number of rows which corresponds to the number of sensors 11 and which pass under them during covering of the transporting track. Thereby each molded blank 3 is scanned. It is also possible to provide less sensors 11 than rows of the molded blanks 3. In each case, the illustration in the drawings is just a principle one and not limiting to the present invention.

The sensors 11 are mounted on their traverse adjustably by displacement.

When a molded blank is located under a sensor 11 which is recognized by a measuring value flank, all five measurement sensors pick up a value and store it. When at the end of the molded blank the measuring value drops, then the measurement is finished. A minimal value, a maximal value and an average value are determined from each measurement and stored.

The average thickness of the molded blank 3 as well as its surface roughness are computed from these values of the preliminarily determined plate thickness and the known height of the laser measuring device 8 over the second transporting device 6. They are compared with preliminarily stored nominal values.

For documentation purposes, all stored values can be preserved. Therefore, it is possible to perform a corresponding production analysis.

For determination of the density of the molded blank 3 its weight must be determined.

For this purpose the weight of each empty plate 4 is determined in a first weighing device 12 arranged in the first transporting device 5. After loading of the plate 4 its weight is determined in a second weighing device 13 arranged in the second transporting device 6.

The weighing devices 12, 13 are substantially identical, but arranged differently. Each weighing device 12, 13 has a weighing cell or pressure cell 14 adjusted also for the non-central force application.

A plate form 18 is located over each pressure cell 14, and the corresponding plate 4 can be placed on the platform. Since the whole arrangement is symmetrical, the resultant is formed from the mass forces of the plate 4 or the molded blank 3 centrally relative to the pressure cell 14. The pressure cell 14 of the type which is utilized here has a resulting error of less than 0.02%. The pressure cell 14 of the first weighing device 12 has a nominal load of 250 kg while the second weighing device 13 has a nominal load of 1.000 kg. The limiting load of each pressure cell 14 amounts to 200% of the nominal load.

The pressure cells are connected in the 6-conductor technique, for compensating long supply conduits and temperature differences.

The pressure cells 14 sit each on a lifting device 15. The lifting device lifts the whole associated weighing device 12, 13 with their platform 18 until over the level of the associated transporting device 5, 6.

When the corresponding plate 4 is located in the proper position over the weighing device 12, 13, it is lifted, engages the plate 4 and lifts it a little. When its own vibrations are eliminated, the weighing process is performed. Subsequently, the weighing device 12, 13 is again loaded by the lifting device 15 until the plate 4 again sits on the transporting device 5, 6.

The measuring accuracy during a release of correspondingly 4095 increments amounts to 61.1 g in the first weighing device 12 and to 244.2 g in the second weighing device 13.

For testing the surface quality an image processing system is provided in accordance with the present invention. In the system one or several preferably two black-white video cameras 16 are utilized which take up an image of the molded blank 3 located under them or passing under them with a predetermined speed. The taken up images are compared with the stored images of errors with consideration of permissible tolerances.

The image taking is performed in an illumination tunnel 17 which excludes outside influences.

The video camera 16 and a suitable illumination are accommodated in the tunnel. A fluorescent pipe extending transversely to the transporting direction of the plate 4 and over its whole width can be used as the illumination. It illuminates the molded blank 3 under a flat angle which makes visible unevenness in a contrasting manner.

The tunnel 17 is movable over the second transporting device 6 and therefore it suitable to move together with the plate 4 when it moves. Moreover, the movable tunnel 17 is designed so that it can ride over different regions correspondingly of the one plate 4 and thereby the video image taking is possible for several molded blanks 3 located on it. Therefore the failure resolution is improved.

Preferably, a first image is taken of the forward half of a plate 4 and supplied to processing. When the image data are no longer required, the tunnel 17 moves over the rear half of the same plate 4 and takes up an image which is also processed. Independently from the image processing, it is advantageous to show each image in rotation or immovably for monitoring by personnel.

In the illustrated and described device the occurrence of a tolerance excess can be brought to the attention of the personnel by indication on a monitor, and can additionally or instead of it release a process control which counteracts the tolerance excess.

Moreover, it is possible to provide an identification device with which each rejected plate is identified by placing a marking body on the corresponding plate 4. Therefore, the plates 4 with faulty molded blanks 3 can be immediately identified when they are transported further by the second transporting device 6 to a dryer and there discharged by a special position regulation. Such a signal body can be however recognized by a weighing control which rejects the plates 4 with faulty molded blanks at an arbitrary point of the transporting device 6.

It is also possible to incorporate the above illustrated and described devices into a total process control.

It will be understood that each of the elements described above, or two or more together, may also find a useful application in other types of methods and constructions differing from the types described above.

While the invention has been illustrated and described as embodied in a method of and apparatus for quality control during production of concrete blocks, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A method of producing concrete blocks with predetermined strength and chemical resistance, comprising the steps of weighing conveyed supporting boards individually; determining a lower level of a supporting surface of each of the supporting boards at a plurality of locations; rejecting the supporting boards as being inappropriate when lower level differences at the plurality of locations surpass a predetermined limit; putting several molded blanks on the supporting surface of a non-rejected supporting board, which molded blanks have been made by introducing fresh concrete into hollow molds with fixed circumferential walls; weighing the non-rejected supporting board carrying the molded blanks; determining an upper level of upper boundaries of the molded blanks; calculating a density of the molded blanks by using a difference of the lower and upper levels, a known value of a circumference of the molded blanks, and a weight difference of the supporting board with and without the molded blanks thereon; and comparing the calculated density with a predetermined value, which predetermined value is related to a predetermined strength and chemical resistance of the concrete blocks which results after curing of said molded blanks thus providing for control of the production of the concrete blocks with the predetermined strength and chemical resistance.

2. A method as defined in claim 1, wherein said steps of determining the levels is performed in a contact-free manner.

3. A method as defined in claim 1; and further comprising the steps of imparting to the supporting surface a first relative movement toward a first position measuring sensor device, and during this performing several individual position measurements, and using their average value for determining a thickness of a concrete block.

4. A method as defined in claim 3; and further comprising the step of considering the supporting surface as non-useable when a maximal difference of the individual position measurements exceeds a predetermined limiting value.

5. A method as defined in claim 3; and further comprising the step of a second relative movement of the supporting surface toward the first measuring sensor device during performing of the individual position measurements.

6. A method as defined in claim 3, wherein said step of individual position measurements are performed at locations which are offset relative to one another.

7. A method as defined in claim 3, wherein said steps of individual position measurements are performed by ultrasound measurements.

8. A method as defined in claim 1; and further comprising the steps of imparting a second relative movement to the supporting surface toward a second position measuring sensor device.

9. A method as defined in claim 8, wherein the putting includes arranging several molded blanks near one another transversely to the second relative movement on the supporting surface; and scanning the several molding blanks simultaneously by several measuring sensor devices.

10. A method as defined in claim 9, wherein said measuring sensor devices are devices for performing laser measurements.

11. A method as defined in claim 8, wherein the putting includes arranging several molded blanks one behind the other in direction of the second relative movement on the supporting surface, and scanning the several molded blanks one after the other by a same measuring sensor device.

* * * * *